US00PP17045P2

(12) United States Plant Patent
Friday

(10) Patent No.: US PP17,045 P2
(45) Date of Patent: Aug. 22, 2006

(54) PEACH TREE NAMED 'P.F. 7A FREESTONE'

(50) Latin Name: *Prunus persica*
Varietal Denomination: P.F. 7A Freestone

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 0 days.

(21) Appl. No.: 10/980,811

(22) Filed: Nov. 4, 2004

(51) Int. Cl.
*A01H 5/00* (2006.01)

(52) U.S. Cl. ..... Plt./198
(58) Field of Classification Search ..... Plt./198
See application file for complete search history.

(56) References Cited

U.S. PATENT DOCUMENTS

PP9,895 P * 5/1997 Friday ..... Plt./198
PP15,498 P2 * 1/2005 Friday ..... Plt./198

OTHER PUBLICATIONS http://www.flaminfury.com/?action=147 Paul Friday's Famin' Fury Peaches Testimonials.*
http://www.flaminfury.com/?action=149 Paul Friday's Flamin' Fury Peaches Flamin' Fury Varieties.*

* cited by examiner

*Primary Examiner*—W. C. Haas

(57) ABSTRACT

A new and distinct variety of peach tree having the following unique combination of desirable features.

1. Producing a very firm fruit having a resilient flesh texture.
2. Blossoms are showy when in full bloom.
3. A substantially spheroidal fruit with an attractive red skin coloring over a majority of the surface.
4. An early maturing fruit that is freestone.
5. An early maturing fruit of good taste.

1 Drawing Sheet

Botanical classification: *Prunus persica.*
Variety denomination: 'P.F. 7A Freestone'.

ORIGIN OF VARIETY

The new peach tree (hereinafter referred to as the 'P.F. 7A Freestone' peach tree) was originated by Paul Friday in an experimental orchard, which is maintained for the purposes of breeding peach trees, located in Coloma, Mich. Coloma is located in the southwest section of Michigan, USDA Hardiness Zone 6a, with observed temperature ranges of minus 12 degree Fahrenheit to 90 degree Fahrenheit, also annual rainfall of about 40 inches.

In an ongoing mass selection breeding program, unpatented superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollinations of the trees in the experimental orchard are regularly planted in mass to produce new populations of seedlings, which are cultured and monitored to maturity. Trees with superior attributes are retained for further observation and testing, and contribute seeds to advancing generations of new populations of seedlings.

The tree of this application 'P.F. 7A Freestone', was a single plant from one such a unpatented seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF VARIETY

The new and distinct variety of peach tree was asexually propagated by budding as performed in an experimental orchard located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of moderate upright growth and a regular bearer of peaches. The blossoms are characterized by being spread when in full bloom.

The blossoms of the present peach tree at full bloom may be characterized as being showy. More specifically, the blossom of the present peach tree have angularly spaced five (5) petals projecting upwardly at an inclined angle so as to form a blossom having a diameter of about 1½" measured across the blossoms. The typical shown blossom as exemplified by the 'Loring' (unpatented) peach.

The flesh of the fruit of the present peach tree is firm and is yellow.

The skin is smooth and is of dark color over about ninety (90%) percent of its surface at maturity. The red color occurs over about sixty (60%) percent of the surface 10 days prior to maturity. At maturity the peach is substantially spherodial with the diameter ranging between about 2½" and 2¾".

The fruit has a firm flesh and may be described as resilient to the extent that the flesh is yieldable and restorable to its original state when subjected to impact forces which may cause permanent deformities in peaches of commercial varieties. The firmness of the fruit facilitates handling and packaging of the peaches without damaging the same for shipment. This results in less spoilage and also increases the shelf life.

The fruit matures in the early part of the peach-growing season of southwestern Michigan. The fruit as mentioned heretofore is of red color over about ninety (90%) percent of its spherodial surface and has a very attractive appearance.

BRIEF DESCRIPTION OF THE PHOTOGRAPHS

The accompanying photographic illustrations of a 7 year old tree of the new variety show the following:

The top photograph depicts three (3) well-rounded fruit showing an unpronounced suture and a well rounded blossom end. One specimen of the fruit is bisected at a ninety-degree angle to the plane of the suture with the stone retained in half showing its freestone characteristic and clear yellow flesh and a minimum of red around the pit. A tape measure is present indicating the large size of the fruit.

The bottom photograph depicts leaves of medium length and width, having notably very fine serrated margins. A tape measure is present, demonstrating the medium size of the leaves.

DESCRIPTION OF VARIETY

The detailed botanical descriptions of the foliage and fruit of the new variety of peach tree is based upon observations of a 7 year old specimen grown on its own roots at Coloma, Mich. USDA Zone 6a, with the color terminology, other than the terminology expressed in common terms, in accordance with the Pantone Matching System (PMS) as used internationally to identify printed colors.

Botanical classification: *Prunus persica* cultivar 'P.F. 7A Freestone'.

Tree:
- *Age.*—Seven (7) years.
- *Height.*—Unpruned 11'.
- *Width.*—Unpruned 10'.
- *Size.*—Medium.
- *Vigor.*—Vigorous.
- *Density.*—Medium — moderate pruning required.
- *Form.*—Moderately upright.
- *Production.*—Good (produces about 1 bushel per tree per year).
- *Bearer.*—Consistent bearer.
- *Disease resistance to bacterial leaf and fruit spot.*—Very good.
- *Rootstock.*—Grown on its own roots.

Trunk:
- *Bark.*—Gray (pantone # 436).
- *Size.*—Medium.
- *Surface.*—Smooth.
- *Diameter.*—3" — at a height of 18" above ground.
- *Lenticels.*—Smooth.
- *Lenticels color.*—Reddish tan (pantone # 156).
- *Lenticels size.*—3/16".

Branches:
- *Size.*—Medium — 1½" diameter at 4" from trunk union.
- *Surface.*—Smooth.
- *Lenticels per square inch on branch.*—Eight (8).
- *Lenticels color.*—Reddish tan (pantone # 156).
- *Lenticels size.*—3/16".
- *Crotch angles.*—Natural right angles.
- *Branch color.*—Gray (pantone # 436).
- *Internodes length.*—½".

Leaves:
- *Size.*—Average length 7¾", average width 1⅝".
- *Color.*—Top of leaf dark green (pantone # 371) bottom of leaf green (pantone # 378).
- *Form.*—Lanceolate — pointed.
- *Thickness.*—Medium.
- *Texture.*—Glabrous.
- *Margin.*—Finely serrated.
- *Petiole length.*—½".
- *Gland.*—Average 2 on each side of petiole (located very close to top, they are also unusually raised above petiole surface).
- *Gland color.*—Green.
- *Gland shape.*—Extremely small, cupped, and notably located on the top side of petiole.

Flower buds:
- *Size.*—⅜" long — 3/16" wide.
- *Shape.*—Ovoid.
- *Color.*—Pink (pantone # 218).

Flowers:
- *Blooming period.*—Apr. 15, 2004 to Apr. 21, 2004.
- *Bloom size.*—1 7/16" diameter.
- *Bloom depth.*—7/16" deep.
- *Size of petals.*—⅞" long — 11/16" wide.
- *Shape of petals.*—Ovate.
- *Number of petals.*—Five (5).
- *Petal margin.*—Smooth (entire).
- *Petal base.*—Pointed.
- *Petal apex.*—Rounded.
- *Petal color.*—Top of petal Pink (pantone # 218) Bottom of petal Pink (pantone # 230).
- *Sepal size.*—¼" long — 3/16" wide.
- *Sepal shape.*—Ovate.
- *Sepal color.*—(Pantone # 383).
- *Sepal margin.*—Entire.
- *Sepal base.*—Rounded.
- *Sepal apex.*—Pointed.
- *Number of sepals.*—Five (5).
- *Number of anthers.*—Twenty six (26).
- *Anther color.*—(Pantone # 154).
- *Number of stamens.*—Twenty six (26).
- *Stamen color.*—(Pantone # 226).
- *Pistil length.*—½".
- *Pistil color.*—(Pantone # 110).
- *Pollen.*—Present, self-fertilizing.
- *Flower color.*—Pink (pantone # 218).
- *Flowers per cluster.*—2–3.
- *Fragrance.*—None — noticeable.

Fruit:
- *Maturity when described.*—Firm ripe.
- *Date of first picking.*—Jul. 12, 2004.
- *Date of last picking.*—Jul. 23, 2004.
- *Size.*—Average diameter 2 9/16".
- *Form.*—Spherical.
- *Suture.*—Not pronounced.
- *Weight.*—7.7 oz.

Skin:
- *Thickness.*—Medium as compared to the species.
- *Texture.*—Medium as compared to the species.
- *Tendency to crack.*—None.
- *Down.*—Shorter & less than is typical.

*Color.*—Red (pantone # 187) over ninety (90%) percent — yellow ground color (pantone # 127).

Flesh:

*Texture.*—Firm non-melting.

*Ripens.*—Evenly.

*Flavor.*—Very good (sugar content was tested at 12% brix).

*Aroma.*—Pleasant.

*Eating quality.*—Very good.

*Brix.*—Average 12%.

*Color.*—Yellow (pantone # 141).

*Pit cavity color.*—Yellow (pantone # 141).

Stone:

*Type.*—Freestone.

*Size.*—1⅜" long, 1" wide, ⅞" thick.

*Form.*—Ovoid.

*Base.*—Straight.

*Apex.*—Pointed.

*Sides.*—Uneven.

*Surface.*—Furrowed.

*Color.*—Tan (Pantone # 475).

*Tendency to crack.*—None.

*Kernel.*—9/16" long, 3/16" wide, 1/16" thick.

*Kernel taste.*—Bland taste.

Use: Dessert.

Shipping quality: Good.

Keeping quality: Good (up to 3 weeks).

Disease resistance: The fruit is resistant to brown rot, and bacterial spot.

The tree and its fruit herein described may vary in slight detail as a result of differences in climatic or soil conditions or cultural practices under which the tree may be grown. It is understood that the description of the new variety as set forth herein is that of the tree grown under the ecological conditions prevailing at Coloma, Mich.

What is claimed is:

1. A new and distinct variety of peach tree substantially as herein illustrated and described.

* * * * *

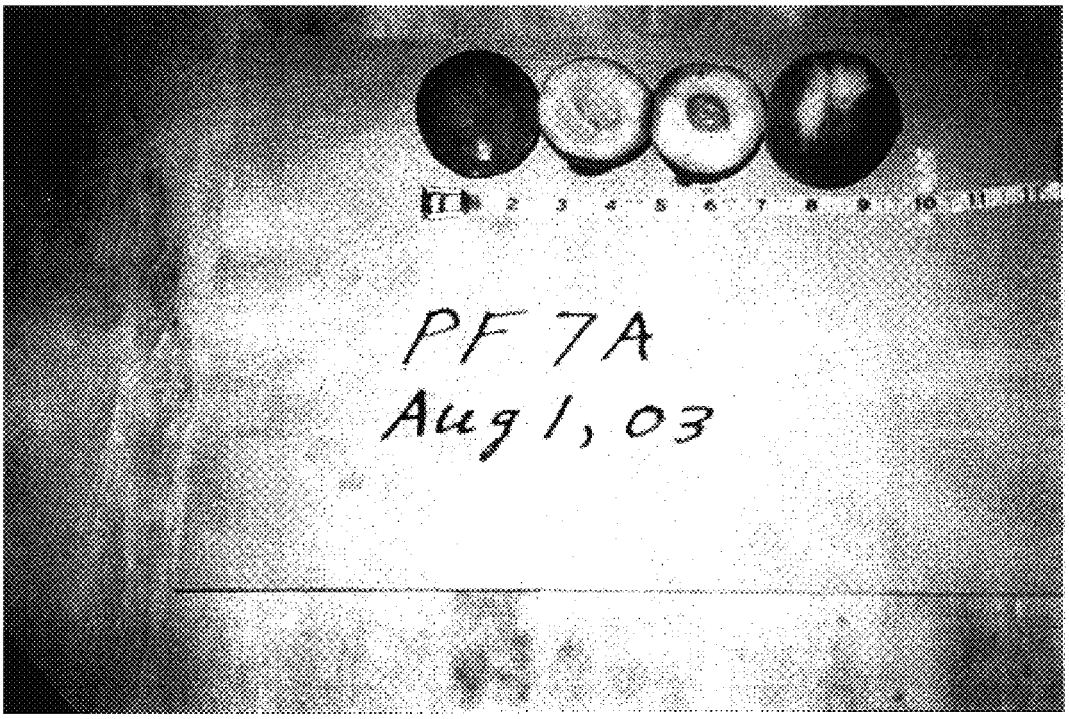
PF 7A
Aug 1, 03
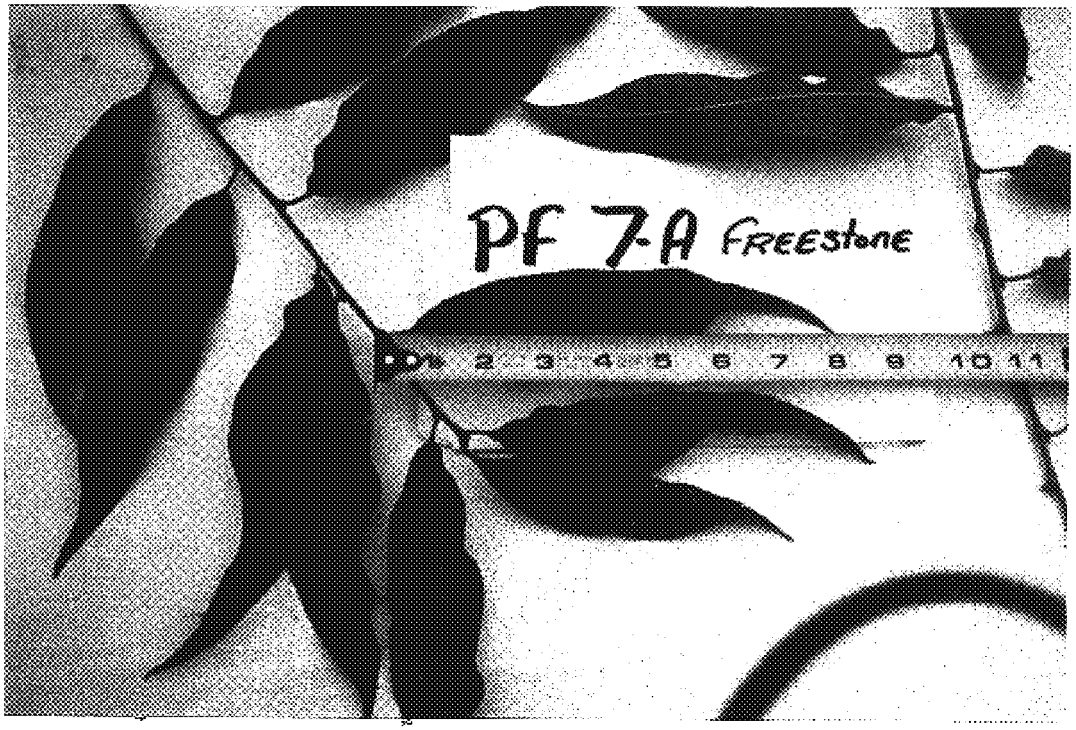
PF 7-A FREESTONE